United States Patent [19]

Ishimitsu et al.

[11] Patent Number: 5,304,566
[45] Date of Patent: Apr. 19, 1994

[54] PYRIDINE COMPOUNDS WHICH HAVE USEFUL INSECTICIDAL UTILITY

[75] Inventors: Keiichi Ishimitsu; Junji Suzuki; Haruhito Ohishi; Tomio Yamada; Renpei Hatano; Nobuo Takakusha; Jun Mitsui, all of Odawara, Japan

[73] Assignee: Nippon Soda Co., Ltd, Chiyoda, Japan

[21] Appl. No.: 700,165
[22] PCT Filed: Oct. 4, 1990
[86] PCT No.: PCT/JP90/01282
§ 371 Date: Jul. 9, 1991
§ 102(e) Date: Jul. 9, 1991
[87] PCT Pub. No.: WO91/04965
PCT Pub. Date: Apr. 18, 1991

[30] Foreign Application Priority Data

Oct. 6, 1989 [JP] Japan .................. 1-259966
Dec. 27, 1989 [JP] Japan .................. 2-56611
May 2, 1990 [JP] Japan .................. 2-115246
Jul. 26, 1990 [JP] Japan .................. 2-196258

[51] Int. Cl.$^5$ ............. C07D 213/36; A01N 43/36
[52] U.S. Cl. .................. 514/357; 546/286; 546/300; 546/311; 546/329; 546/332; 546/334; 546/338; 514/344; 514/345; 514/352
[58] Field of Search .............. 546/330, 286, 300, 311, 546/329, 332, 334, 338; 514/357, 344, 345, 352

[56] References Cited

U.S. PATENT DOCUMENTS 4,918,088 4/1990 Gsell .................. 546/333

OTHER PUBLICATIONS

Hackh's Chemical Dictionary, p. 62, 1969.
Del Corona et al, *Boll. Chim. Farm*, vol. 118 (11), pp. 661–666 (1979).
Chemical Abstracts, vol. 115 (9), Abstract No. 92.085a, p. 745, Sep. 2, 1991.

*Primary Examiner*—C. Warren Ivy
*Assistant Examiner*—Zinna N. Davis
*Attorney, Agent, or Firm*—Joseph C. Mason, Jr.; George Oujevolk; Ronald E. Smith

[57] ABSTRACT

The present invention relates to a compound having the formula below which has an excellent insecticidal activity:

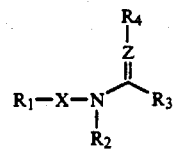

wherein $R_1$ represents an optionally substituted 5-6 membered aromatic hetero ring containing nitrogen atom, except a non-substituted 2-pyridyl; x represents an optionally substituted $C_{1-3}$ alkylene $R_2$ represents a hydrogen, a carbamoyl, a mono or di $C_{1-5}$ alkyl carbamoyl, a thiocarbamoyl, a mono or di $C_{1-5}$ alkylthiocarbamoyl, a sulfamoyl, a mono or di $C_{1-5}$ alkylsulfamoyl, an optionally substituted $C_{1-5}$ alkyl, an optionally substituted $C_{2-5}$ alkenyl, an optionally substituted $C_{2-5}$ alkynyl, an optionally substituted $C_{3-8}$ cycloalkyl, an optionally substituted $C_{3-8}$ cycloalkenyl, an optionally substituted aryl or $-Y-R_5$;

Y represents O, $S(O)_n$, CO, CS or $CO_2$;

n represents 0, 1 or 2;

$R_5$ represents a hydrogen, an optionally substituted $C_{1-5}$ alkyl, an optionally substituted $C_{2-5}$ alkenyl, an optionally substituted $C_{2-5}$ alkynyl, an optionally substituted $C_{3-8}$ cycloalkyl, an optionally substituted $C_{3-8}$ cycloalkenyl or an optionally substituted aryl;

$R_3$ represents a hydrogen, an optionally substituted $C_{1-5}$ alkyl, an optionally substituted $C_{2-5}$ alkenyl, an optionally substituted $C_{2-5}$ alkynyl, an optionally substituted $C_{3-8}$ cycloalkyl or an optionally substituted $C_{3-8}$ cycloalkenyl; $R_4$ represents a cyano or a nitro; and Z represents CH or N; or its salt.

16 Claims, No Drawings

PYRIDINE COMPOUNDS WHICH HAVE USEFUL INSECTICIDAL UTILITY

FIELD OF INVENTION

The present invention relates to new amine derivatives, the processes for the production thereof and insecticides containing the said derivatives as effective compounds.

DESCRIPTION OF RELATED ART

A large number of chemicals, for example, organophosphorus compounds such as parathion and malathion and carbamate compounds such as carbaryl and methomyl, have been developed and put to practical use as insecticides over many years. These insecticides have played a very great role for the improvement of agricultural production. However, in recent years some of these insecticides are regulated on their use because of problems such as environmental pollution due to residue or accumulation, or cause infestation of resistant insect pests as a result of long-term use. Therefore, there is a need to develop new chemicals which have excellent insecticidal characteristics over various types of insect pests including these resistant insect pests and which can be used safely.

The following compound is known as the isomer compound of this invention, which has no insecticidal activity.

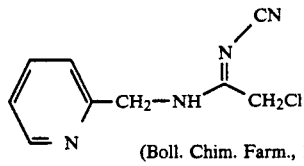

(Boll. Chim. Farm., 1979 118(11)661-666)

Further, the following compound is described in U.S. Pat. No. 4,918,088, which has insecticidal activities.

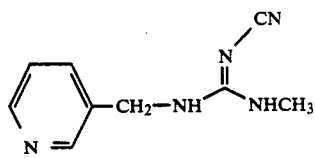

The compound however shows no insecticidal activity against lepidopterous insects and green rice leafhopper which are more serious pests on crops, though it shows some activity against cotton aphid.

The purpose of this invention is to provide agricultural chemicals which can be advantageously synthesized industrially, have certain effects and may be applied safely.

The compound of this invention has high insecticidal activity against both lepidopterous and hemipterous insects.

SUMMARY OF THE INVENTION

The present invention relates to a compound having the formula

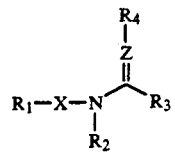

wherein $R_1$ represents an optionally substituted 5-6 membered aromatic hetero ring containing nitrogen atom, except a nonsubstituted 2-pyridyl;

X represents an optionally substituted $C_{1-3}$ alkylene or alkylidene;

$R_2$ represents a hydrogen, a carbamoyl, a mono or di $C_{1-5}$ alkyl carbamoyl, a thiocarbamoyl, a mono or di $C_{1-5}$ alkylthiocarbamoyl, a sulfamoyl, a mono or di $C_{1-5}$ alkylsulfamoyl, an optionally substituted $C_{1-5}$ alkyl, an optionally substituted $C_{2-5}$ alkenyl, an optionally substituted $C_{2-5}$ alkynyl, an optionally substituted $C_{3-8}$ cycloalkyl, an optionally substituted $C_{3-8}$ cycloalkenyl, an optionally substituted aryl or $-Y-R_5$;

Y represents O, $S(O)_n$, CO, CS or $CO_2$;

n represents 0, 1 or 2;

$R_5$ represents a hydrogen, an optionally substituted $C_{1-5}$ alkyl, an optionally substituted $C_{2-5}$ alkenyl, an optionally substituted $C_{2-5}$ alkynyl, an optionally substituted $C_{3-8}$ cycloalkyl, an optionally substituted $C_{3-8}$ cycloalkenyl or an optionally substituted aryl;

$R_3$ represents a hydrogen, an optionally substituted $C_{1-5}$ alkyl, an optionally substituted $C_{2-5}$ alkenyl, an optionally substituted $C_{2-5}$ alkynyl, an optionally substituted $C_{3-8}$ cycloalkyl or an optionally substituted $C_{3-8}$ cycloalkenyl;

$R_4$ represents a cyano or a nitro; and Z represents CH or N; or its salt.

DESCRIPTION OF THE PREFERRED EMBODIMENTS

The compounds of this invention can be prepared in accordance with the following reaction schemes:

(1) Preparation Method 1:

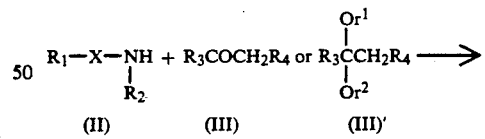

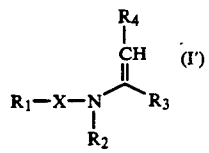

where $r^1$ and $r^2$ represent a $C_{1-5}$ alkyl; and $R_1$, $R_2$, $R_3$, $R_4$ and X are as defined above.

The reaction is carried out in an inactive organic solvent, preferably in an aromatic hydrocarbon solvent such as xylene, toluene or benzene, in the presence of acidic catalyst such as p-toluenesulfonic acid, if necessary, under reflux.

(2) Preparation method 2:

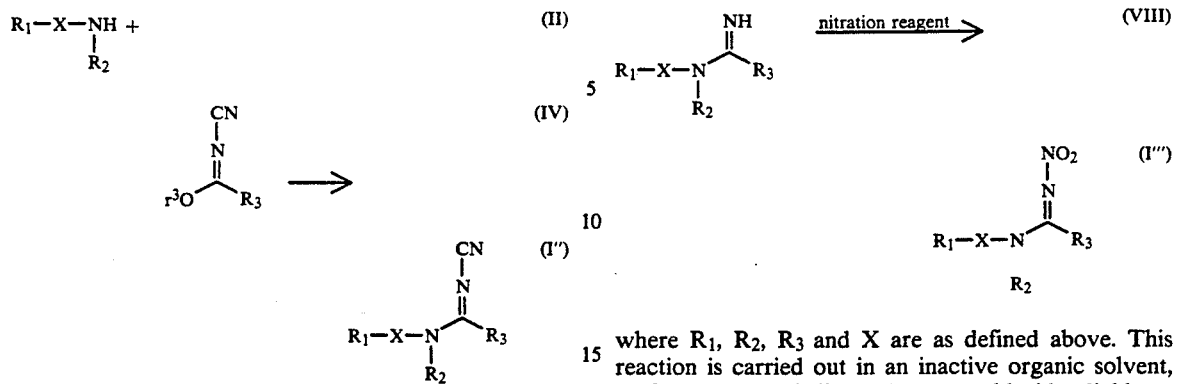

where $r^3$ represents a $C_{1-5}$ alkyl: and $R_1$, $R_2$, $R_3$ and X are as defined above. This reaction is carried out in an inactive organic solvent, preferably in an alcohol such as methanol, ethanol, between room temperature and the boiling point of the used solvent.

(3) Preparation Method 3:

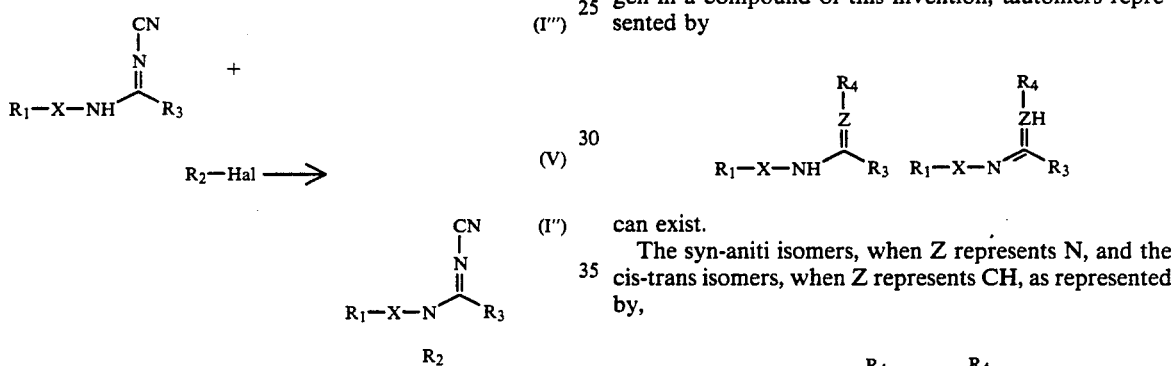

where Hal represents a halogen; and $R_1$, $R_2$, $R_3$ and X are as defined above. This reaction is carried out in an inactive organic solvent, preferably DMF, THF, benzene acetonitrile, acetone, methylethylketone, in the presence of acid accepter such as potassium carbonate, NaH, triethylamine, between room temperature and the boiling point of the used solvent.

(4) Preparation Method 4:

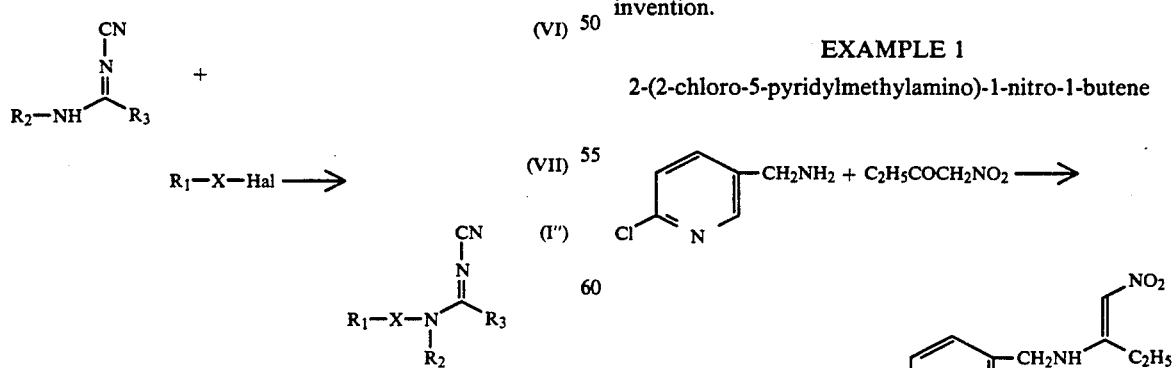

where $R_1$, $R_2$, $R_3$, X and Hal are as defined above. This reaction is carried out in the same manner as that of Preparation Method 3.

(5) Preparation Method 5:

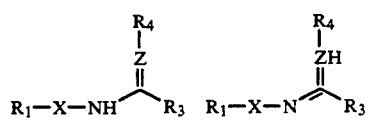

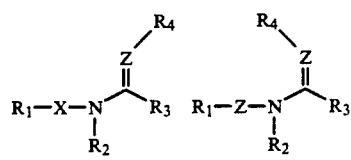

where $R_1$, $R_2$, $R_3$ and X are as defined above. This reaction is carried out in an inactive organic solvent, preferably acetonitrile, carbon tetrachloride, dichloroethane, in the presence of nitration reagent such as nitronium tetrafluoroborate, between $-20°$ C. and the boiling point of the used solvent.

After the reaction is completed, an usual after-treatment gives the intended compound. The structure of the compounds of this invention was determined by such means as IR, NMR, MASS, etc. When $R_2$ is hydrogen in a compound of this invention, tautomers represented by

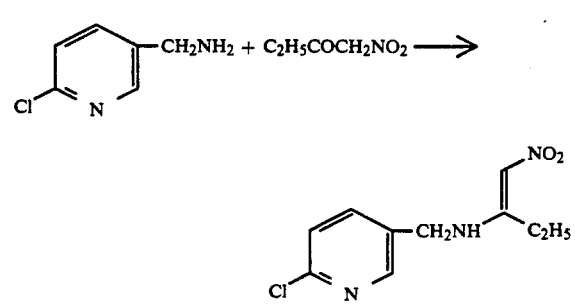

can exist.

The syn-aniti isomers, when Z represents N, and the cis-trans isomers, when Z represents CH, as represented by, can also exist.

The ratio varies depending on e.g. conditions of instrumental analysis.

The following EXAMPLES illustrate the present invention.

EXAMPLE 1

2-(2-chloro-5-pyridylmethylamino)-1-nitro-1-butene

In 50 ml of toluene, 4.2 g of 2-chloro-5-pyridylmethylamine, 3.5 g of 1-nitro-2-butanone and 0.1 g of p-toluene sulfonic acid were mixed and the mixture was refluxed for 2 hours. The solvent was then distilled off and the residue was purified by column chromatography on silica gel to afford 4.1 g of compound No. 368. m.p. 95°–98° C.

EXAMPLE 2

2-(2-chloro-5-pyridylmethylamino)-1-cyano-1-propene

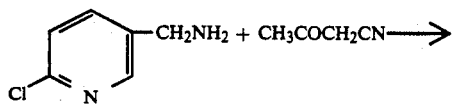

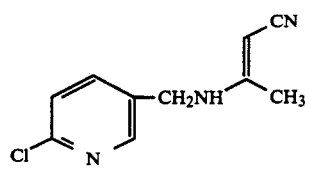

1.4 g of 2-chloro-5-pyridylmethylamine and 0.8 g of 1-cyano-2-propanone were mixed and the mixture was stirred at room temperature over night. The solvent was then distilled off and the residue was purified by column chromatography on silica gel to afford 1.7 g of compound No. 528. m.p. 95°–98° C.

EXAMPLE 3

N-cyano-N'-(2-chloro-5-pyridylmethyl)-N'-methylacetamidine

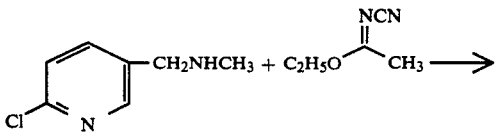

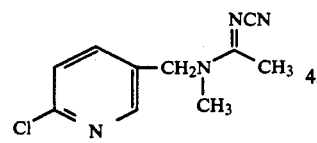

In 20 ml of ethanol, 1.6 g of N-methyl-2-cloro-5-pyridylmethylamine and 1.2 g of ethyl-N-cyanoacetamidine were mixed and the mixture was stirred at room temperature over night. The solvent was then distilled off and the residue was purified by column chromatography on silica gel to afford 1.8 g of compound No. 22. m.p. 101°–103° C.

EXAMPLE 4

N-cyano-N'-(2-chloro-5-pyridylmethyl)-N'-ethylacetamidine

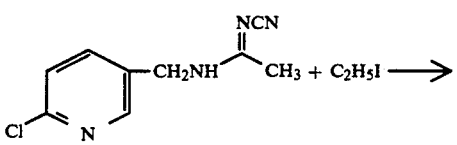

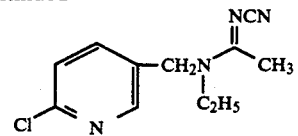

0.7 g of sodium hydride (purity 60%) was added to the solution of 3.0 g of N-cyano-N'-(2-chloro-5-pyridylmethyl)acetamidine in 20 ml of N.N-dimethylformamide at ice bath temperature. After stirring it at the same temperature for 1 hour, 2.7 g of ethyl iodide was added to the mixture, followed by stirring for 5 hours at room temperature. The reaction mixture was then poured into ice-water, extracted with ethyl acetate, dried over anhydrous magnesium sulfate and concentrated under reduced pressure. The residue obtained was purified by column chromatography on silica gel to afford 1.6 g of compound No. 51. m.p. 100°–101° C.

EXAMPLE 5

N-cyano-N-(2-chloro-5-pyridylmethyl)-N'-methylacetamidine

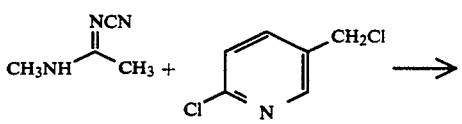

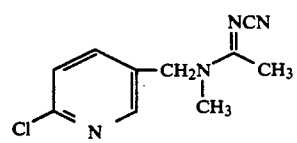

0.6 g of sodium hydride (purity 60%) was added to the solution of 1.3 g of N-cyano-N'-methylacetamidine in 20 ml of N,N-dimethylformamide at ice bath temperature. After stirring it at the same temperature for 1 hour, 2.2 g of 2-chloro-5-pyridylmethylchloride was added to the mixture, followed by stirring for 5 hours at room temperature. The reaction mixture was then poured into ice-water, extracted with ethyl acetate, dried over anhydrous magnesium sulfate and concentrated under reduced pressure. The residue obtained was purified by column chromatography on silica gel to afford 1.5 g of compound No. 22 m.p. 101°–103° C.

REFERENCE EXAMPLE

N-(2-chloro-5-pyridylmethyl)-N-methylacetamidine hydrochloride

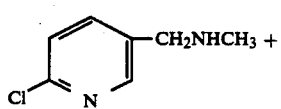

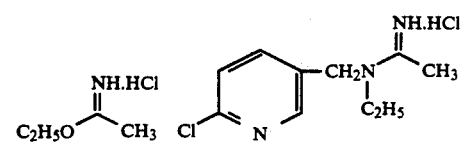

To 40 ml of ethanol was added 5.1 g of N-(2-chloro-5-pyridylmethyl)-N-Methylamine and then 4 g of ethyl acetimidate hydrochloride at 0° C. After stirring for an hour, the reaction mixture was allowed to warm to room temperature and stirred over night. The solvent was then distilled off. The obtained white residue was washed with diethyl ether to afford 7.3 g of the title compound m.p. 192°–197° C.

EXAMPLE 6

N-(2-chloro-5-pyridylmethyl)-N-methyl-N'-nitroacetamidine

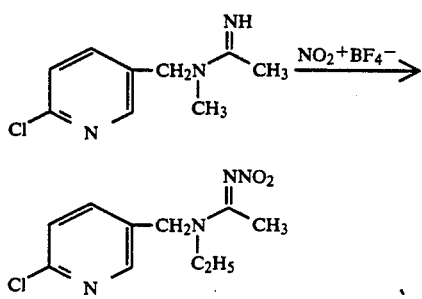

To a suspension of 1 g of N-(2-chloro-5-pyridylmethyl)-N-methylamidine hydrochloride in 10 ml of dry acetonitrile was added dropwise 0.7 g of DBU under nitrogen at room temperature. After stirring for 30 minutes, the solution was added dropwise to a suspension of 0.6 g of nitronium tetrafluoroborate in 5 ml of dry acetonitrile under nitrogen on cooling with ice-water and let stir for 4 hours. After which time, the mixture was poured into ice-water, then extracted several time with chloroform. The combined chloroform layer was dried over magnesium sulfate, filtered and distilled off. The crude oil was purified by column chromatgraphy on silica gel to afford 0.3 g of compound No. 236.

$N_D^{25}$ 1.5808.

Typical examples of this invention including those described above are listed in Table 1.

TABLE 1

Structure Formula $$R_1X-N(R_2)-C(R_3)=Z-R^4$$

| Compound No. | $R_1X$ | $R_2$ | $R_3$ | Z | $R_4$ | Physical Properties [ ] m.p. °C. |
|---|---|---|---|---|---|---|
| 1 | 2-chloro-5-pyridyl-CH$_2$– | H | H | N | CN | [123–126] |
| 2 | " | " | CH$_3$ | " | " | [141–143] |
| 3 | " | " | CH$_2$Cl | " | " | [124–126] |
| 4 | " | " | CH$_2$F | " | " | [151–152] |
| 5 | " | " | CF$_3$ | " | " | [112–114] |
| 6 | " | " | C$_2$H$_5$ | " | " | [120–122] |
| 7 | " | " | C$_3$H$_7$(n) | " | " | [100–101] |
| 8 | " | " | cyclopropyl | " | " | [193.5–195] |
| 9 | " | " | C$_4$H$_9$(t) | " | " | |
| 10 | " | " | CH$_2$OCH$_3$ | " | " | [128–128.5] |
| 11 | " | " | CH$_2$SCH$_3$ | " | " | [116–118] |
| 12 | 2-chloro-5-pyridyl-CH$_2$– | H | CH$_2$COOC$_2$H$_5$ | N | CN | $n_D^{25.5}$ 1.5608 |
| 13 | " | " | CH$_2$CH$_2$COOC$_2$H$_5$ | " | " | |
| 14 | " | " | CH$_2$NHCH$_3$ | " | " | |
| 15 | " | " | CH$_2$N(CH$_3$)$_2$ | " | " | |
| 16 | " | " | CH$_2$CH$_2$CH$_2$Cl | " | " | [114–115] |
| 17 | " | " | CH$_2$–C$_6$H$_4$–Cl | " | " | [190–191] |
| 18 | " | " | CH$_2$CN | " | " | [106–108] |
| 19 | " | " | CH$_2$CH$_2$CN | " | " | |

TABLE 1-continued

Structure Formula $$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 20 | " | " | $C_2H_4-C(=NCN)-NH-CH_2-$(6-chloropyridin-3-yl) | " | " | [187–189] |
| 21 | " | CH₃ | H | " | " | $n_D^{25}$ 1.5918 |
| 22 | " | " | CH₃ | " | " | [101–103] |
| 23 | " | " | " | " | " | [161–162] HCl salt |
| 24 | " | " | CH₂Cl | " | " | $n_D^{26.5}$ 1.5921 |
| 25 | " | " | CH₂F | " | " | [79–80] |
| 26 | " | " | CF₃ | " | " | *1 |
| 27 | 6-chloropyridin-3-yl-CH₂— | CH₃ | C₂H₅ | N | CN | $n_D^{27}$ 1.5742 |
| 28 | " | " | C₃H₇(n) | " | " | [97–100] |
| 29 | " | " | cyclopropyl | " | " | $n_D^{24.5}$ 1.5829 |
| 30 | " | " | C₄H₉(t) | " | " | |
| 31 | " | " | CH₂OCH₃ | " | " | $n_D^{24}$ 1.5803 |
| 32 | " | " | CH₂SCH₃ | " | " | $n_D^{24.5}$ 1.6070 |
| 33 | " | " | CH₂COOC₂H₅ | " | " | $n_D^{25.5}$ 1.5604 |
| 34 | " | " | CH₂CH₂COOC₂H₅ | " | " | $n_D^{24.5}$ 1.5605 |
| 35 | " | " | CH₂NHCH₃ | " | " | $n_D^{25}$ 1.5861 |
| 36 | " | " | CH₂N(CH₃)₂ | " | " | $n_D^{25}$ 1.5577 |
| 37 | " | " | CH₂CH₂Cl | " | " | |
| 38 | " | " | CH₂CH₂CH₂Cl | " | " | $n_D^{25.5}$ 1.5830 |
| 39 | " | " | cyclohexyl | " | " | |
| 40 | " | " | —CH₂—phenyl | " | " | |
| 41 | " | " | —CH₂—(4-chlorophenyl) | " | " | $n_D^{25.5}$ 1.6040 |
| 42 | 6-chloropyridin-3-yl-CH₂— | CH₃ | CH=CH₂ | N | CN | |
| 43 | " | " | CH₂CN | " | " | $n_D^{25}$ 1.5913 |

TABLE 1-continued

Structure Formula $$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 44 | " | " | CH₂CH₂CN | " | " | [112–114] |
| 45 | " | " | CH=CH–C₆H₅ | " | " | |
| 46 | " | " | –C₂H₄–C(NCN)(N(CH₃)CH₂-(6-chloropyridin-3-yl)) | " | " | [224–226] |
| 47 | " | CHF₂ | H | " | " | |
| 48 | " | " | CH₃ | " | " | $n_D^{24.5}$ 1.5423 |
| 49 | " | " | C₂H₅ | " | " | |
| 50 | " | C₂H₅ | H | " | " | [101–103] |
| 51 | " | " | CH₃ | " | " | [100–101] |
| 52 | " | " | C₂H₅ | " | " | |
| 53 | " | C₃H₇(i) | H | " | " | [205–207] |
| 54 | " | " | CH₃ | " | " | |
| 55 | " | " | C₂H₅ | " | " | |
| 56 | " | cyclopropyl | H | " | " | |
| 57 | 2-Cl-pyridin-5-yl-CH₂– | cyclopropyl | CH₃ | N | CN | $n_D^{25}$ 1.5825 |
| 58 | " | " | C₂H₅ | " | " | |
| 59 | " | CH₂OCH₃ | H | " | " | |
| 60 | " | " | CH₃ | " | " | $n_D^{25.5}$ 1.5711 |
| 61 | " | CH₂SCH₃ | H | " | " | |
| 62 | " | " | CH₃ | " | " | $n_D^{25}$ 1.5828 |
| 63 | " | CH₂COOC₂H₅ | H | " | " | |
| 64 | " | " | CH₃ | " | " | $n_D^{25}$ 1.5475 |
| 65 | " | CH₂-(furan-2-yl) | H | " | " | |
| 66 | " | " | CH₃ | " | " | $n_D^{25.5}$ 1.5928 |
| 67 | " | CH₂-(thiophen-2-yl) | H | " | " | |
| 68 | " | " | CH₃ | " | " | $n_D^{25.5}$ 1.6155 |
| 69 | " | CH₂-C₆H₅ | H | " | " | |
| 70 | " | " | CH₃ | " | " | $n_D^{24.5}$ 1.6093 |

TABLE 1-continued

Structure Formula $$R_1X-\underset{R_2}{N}-\underset{\|}{\overset{R_4}{\overset{|}{Z}}}{C}-R_3$$

| Compound No. | R₁X | R₂ | R₃ | Z | R₄ | Physical Properties [ ] m.p. °C. |
|---|---|---|---|---|---|---|
| 71 | " | $-CH_2-\underset{}{\text{C}_6H_4}-Cl$ (p) | H | " | " | |
| 72 | 2-Cl-5-pyridyl-CH₂ | $-CH_2-\underset{}{\text{C}_6H_4}-Cl$ (p) | CH₃ | N | CN | [112–114] |
| 73 | " | CH₂CH=CH₂ | H | " | " | $n_D^{25}$ 1.5841 |
| 74 | " | " | CH₃ | " | " | $n_D^{25}$ 1.5809 |
| 75 | " | CH₂C≡CH | H | " | " | |
| 76 | " | " | CH₃ | " | " | $n_D^{25.5}$ 1.5730 |
| 77 | " | CH₂CN | H | " | " | |
| 78 | " | " | CH₃ | " | " | [127–128] |
| 79 | " | $-CH_2-\text{C}_6H_4-OCH_3$ (o) | H | " | " | |
| 80 | " | " | CH₃ | " | " | [124–127] |
| 81 | " | $-CH_2-\text{(6-Cl-3-pyridyl)}$ | H | " | " | |
| 82 | " | " | CH₃ | " | " | $n_D^{24.5}$ 1.6045 |
| 83 | " | $-CH_2-\text{(2-Cl-thiazol-5-yl)}$ | H | " | " | |
| 84 | " | " | CH₃ | " | " | $n_D^{25.5}$ 1.6092 |
| 85 | " | CH₂CH₂-(2-pyridyl) | H | " | " | |
| 86 | 2-Cl-5-pyridyl-CH₂ | CH₂CH₂-(2-pyridyl) | CH₃ | N | CN | $n_D^{25.5}$ 1.5910 |
| 87 | " | CH₂CH₂-C₆H₄-Cl (p) | H | " | " | |
| 88 | " | " | CH₃ | " | " | $n_D^{25.5}$ 1.6162 |

TABLE 1-continued

Structure Formula $$R_1X-N(R_2)-C(R_3)=Z-R_4$$

| Compound No. | $R_1X$ | $R_2$ | $R_3$ | Z | $R_4$ | Physical Properties [ ] m.p. °C. |
|---|---|---|---|---|---|---|
| 89 | " | (phenyl) | H | " | " | |
| 90 | " | " | CH₃ | " | " | [115–117] |
| 91 | " | OCH₃ | H | " | " | |
| 92 | " | " | CH₃ | " | " | [110–112] |
| 93 | " | CHO | H | " | " | |
| 94 | " | " | CH₃ | " | " | |
| 95 | COCH₃ | H | " | " | " | $n_D^{25.5}$ 1.5475 |
| 96 | " | " | CH₃ | " | " | [84–86] |
| 97 | " | SO₂CH₃ | H | " | " | [160–163] |
| 98 | " | " | CH₃ | " | " | |
| 99 | " | (CO–C₆H₄–Cl, 4-chlorobenzoyl) | H | " | " | |
| 100 | " | " | CH₃ | " | " | [112–114] |
| 101 | (6-chloropyridin-3-yl)-CH₂– | COOC₂H₅ | H | N | CN | |
| 102 | " | " | CH₃ | " | " | $n_D^{25}$ 1.5540 |
| 103 | " | CONH₂ | H | " | " | |
| 104 | " | " | CH₃ | " | " | |
| 105 | " | CON(CH₃)₂ | H | " | " | |
| 106 | " | " | CH₃ | " | " | [89–91] |
| 107 | " | CONHCH₃ | H | " | " | |
| 108 | " | " | CH₃ | " | " | |
| 109 | " | CSNHCH₃ | H | " | " | |
| 110 | " | " | CH₃ | " | " | |
| 111 | (6-bromopyridin-3-yl)-CH₂– | H | CH₃ | " | " | |
| 112 | " | CH₃ | " | " | " | |
| 113 | (6-fluoropyridin-3-yl)-CH₂– | H | " | " | " | |
| 114 | " | CH₃ | " | " | " | |
| 115 | (6-methylpyridin-3-yl)-CH₂– | H | " | " | " | [83–85] |

TABLE 1-continued

Structure Formula $$R_1X-N(R_2)-C(R_3)=Z-R^4$$

| Compound No. | R₁X | R₂ | R₃ | Z | R₄ | Physical Properties [ ] m.p. °C. |
|---|---|---|---|---|---|---|
| 116 | 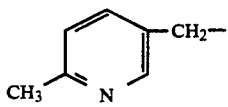 (6-CH₃-pyridin-3-yl-CH₂–) | CH₃ | CH₃ | N | CN | [76–78] |
| 117 | 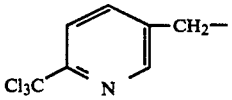 (6-Cl₃C-pyridin-3-yl-CH₂–) | H | " | " | " | |
| 118 | " | CH₃ | " | " | " | [145–147] |
| 119 | 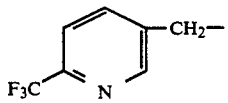 (6-F₃C-pyridin-3-yl-CH₂–) | H | " | " | " | |
| 120 | " | CH₃ | " | " | " | $n_D^{25}$ 1.5202 |
| 121 | 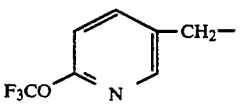 (6-F₃CO-pyridin-3-yl-CH₂–) | H | " | " | " | |
| 122 | " | CH₃ | " | " | " | |
| 123 | 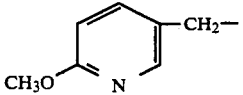 (6-CH₃O-pyridin-3-yl-CH₂–) | H | " | " | " | |
| 124 | " | CH₃ | " | " | " | $n_D^{25.5}$ 1.5580 |
| 125 | 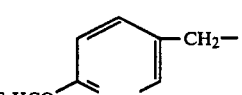 (6-F₂HCO-pyridin-3-yl-CH₂–) | H | " | " | " | |
| 126 | " | CH₃ | " | " | " | |
| 127 | 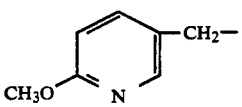 (6-CH₃O-pyridin-3-yl-CH₂–) | H | " | " | " | |
| 128 | " | CH₃ | " | " | " | |
| 129 | 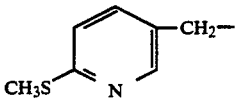 (6-CH₃S-pyridin-3-yl-CH₂–) | H | " | " | " | [162–163] |
| 130 | " | CH₃ | " | " | " | [105–107] |
| 131 | 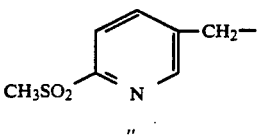 (6-CH₃SO₂-pyridin-3-yl-CH₂–) | H | CH₃ | N | CN | |
| 132 | " | CH₃ | " | " | " | [138–139] |

TABLE 1-continued

Structure Formula $$R_1X-\underset{R_2}{N}-\underset{\|}{C}(R_3)=Z-R_4$$

| Compound No. | R₁X | R₂ | R₃ | Z | R₄ | Physical Properties [ ] m.p. °C. |
|---|---|---|---|---|---|---|
| 133 | ![phenoxy-pyridinyl-CH₂-] (phenyl-O-pyridin-2-yl-5-CH₂–) | H | " | " | " | |
| 134 | " | CH₃ | " | " | " | $n_D^{25}$ 1.5841 |
| 135 | ![NC-pyridinyl-CH₂-] (NC-pyridin-2-yl-5-CH₂–) | H | " | " | " | |
| 136 | " | CH₃ | " | " | " | [107–109] |
| 137 | ![O₂N-pyridinyl-CH₂-] (O₂N-pyridin-2-yl-5-CH₂–) | H | " | " | " | |
| 138 | " | CH₃ | " | " | " | |
| 139 | ![2,4-dichloropyridin-5-yl-CH₂-] | H | " | " | " | |
| 140 | " | CH₃ | " | " | " | |
| 141 | ![6-chloro-2-methylpyridin-3-yl-CH₂-] | H | " | " | " | |
| 142 | " | CH₃ | " | " | " | |
| 143 | ![(CH₃)₂N-pyridin-2-yl-5-CH₂-] | H | " | " | " | [122–124] |
| 144 | " | CH₃ | " | " | " | [110–113] |
| 145 | ![pyrazin-2-yl-CH₂-] | H | CH₃ | N | CN | [66–68] |
| 146 | " | CH₃ | " | " | " | $n_D^{24.5}$ 1.5790 |
| 147 | ![5-chloropyrazin-2-yl-CH₂-] | H | " | " | " | |
| 148 | " | CH₃ | " | " | " | [94–96] |

TABLE 1-continued
Structure Formula
$$\underset{R_2}{\underset{|}{R_1X-N}}\overset{\overset{R^4}{\underset{|}{Z}}}{=}R_3$$
| Compound No. | R₁X | R₂ | R₃ | Z | R₄ | Physical Properties [ ] m.p. °C. |
|---|---|---|---|---|---|---|
| 149 | 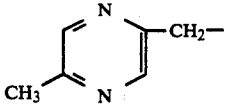 | H | " | " | " | [130–132] |
| 150 | " | CH₃ | " | " | " | $n_D^{25}$ 1.5612 |
| 151 | 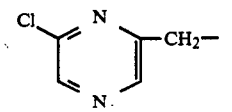 | H | " | " | " | [96–99] |
| 152 | " | CH₃ | " | " | " | $n_D^{25.5}$ 1.5800 |
| 153 | 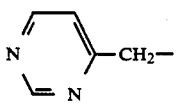 | H | " | " | " | |
| 154 | " | CH₃ | " | " | " | |
| 155 | 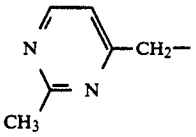 | H | " | " | " | |
| 156 | 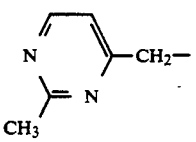 | CH₃ | CH₃ | N | CN | |
| 157 | 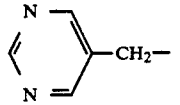 | H | " | " | " | |
| 158 | " | CH₃ | " | " | " | |
| 159 | 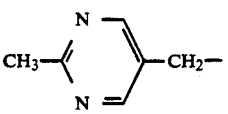 | H | " | " | " | |
| 160 | " | CH₃ | " | " | " | |
| 161 | 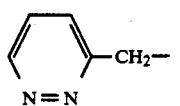 | H | " | " | " | |
| 162 | " | CH₃ | " | " | " | |
| 163 | 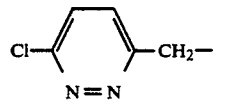 | H | " | " | " | [115–117] |

TABLE 1-continued

Structure Formula $$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 164 | " | CH₃ | " | " | " | $n_D^{23}$ 1.5717 |
| 165 | 3,5-dimethyl-1-methylpyrazol-4-yl-CH₂— | H | " | " | " | [104–106] |
| 166 | " | CH₃ | " | " | " | |
| 167 | thiazol-5-yl-CH₂— | H | CH₃ | N | CN | |
| 168 | " | CH₃ | " | " | " | |
| 169 | 2-methylthiazol-5-yl-CH₂— | H | " | " | " | [112–114] |
| 170 | " | CH₃ | " | " | " | $n_D^{25}$ 1.5413 |
| 171 | 2-chlorothiazol-5-yl-CH₂— | H | " | " | " | [122–124] |
| 172 | " | CH₃ | " | " | " | [143–144] |
| 173 | " | " | C₂H₅ | " | " | $n_D^{25}$ 1.5575 |
| 174 | " | C₂H₅ | CH₃ | " | " | [63–70] |
| 175 | 2-chloro-4-methylthiazol-5-yl-CH₂— | H | " | " | " | [149–151] |
| 176 | " | CH₃ | " | " | " | |
| 177 | 2-chlorothiazol-5-yl-CH₂— | H | H | " | " | [179–183] |
| 178 | " | CH₃ | " | " | " | $n_D^{25}$ 1.5952 |
| 179 | pyridin-3-yl-CH₂CH₂— | H | CH₃ | N | CN | |
| 180 | " | CH₃ | " | " | " | |
| 181 | 6-chloropyridin-3-yl-CH₂CH₂— | H | " | " | " | |
| 182 | " | CH₃ | " | " | " | |

TABLE 1-continued

Structure Formula $$R_1X-N(R_2)-C(R_4)=Z-R_3$$

| Compound No. | R₁X | R₂ | R₃ | Z | R₄ | Physical Properties [ ] m.p. °C. |
|---|---|---|---|---|---|---|
| 183 | 2-pyridyl-CH₂CH₂— | H | " | " | " | |
| 184 | " | CH₃ | " | " | " | |
| 185 | 6-chloro-2-pyridyl-CH₂CH₂— | H | " | " | " | |
| 186 | " | CH₃ | " | " | " | |
| 187 | 6-chloro-5-pyridyl-CH(CH₃)— | H | " | " | " | |
| 188 | " | CH₃ | " | " | " | [106–109] |
| 189 | 4-pyridyl-CH₂— | H | CH₃ | " | " | [90–92] |
| 190 | 4-pyridyl-CH₂— | CH₃ | CH₃ | N | CN | [102–103] |
| 191 | 5-chloro-2-pyridyl-CH₂— | H | " | " | " | |
| 192 | " | CH₃ | " | " | " | |
| 193 | 3-pyridyl-CH₂— | H | H | " | " | |
| 194 | " | " | CH₃ | " | " | [127–129] |
| 195 | " | " | CH₂Cl | " | " | |
| 196 | " | " | CH₂F | " | " | |
| 197 | " | " | C₂H₅ | " | " | |
| 198 | " | " | cyclopropyl | " | " | |
| 199 | " | " | CH₂SCH₃ | " | " | |
| 200 | " | " | CH₂OCH₃ | " | " | |
| 201 | 3-pyridyl-CH₂— | H | C₃H₇(n) | N | CN | $n_D^{25.5}$ 1.5528 |
| 202 | " | CH₃ | H | " | " | |
| 203 | " | " | CH₃ | " | " | $n_D^{25.5}$ 1.5798 |

TABLE 1-continued

Structure Formula $$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 204 | " | " | CH₂Cl | " | " | |
| 205 | " | " | CH₂F | " | " | |
| 206 | " | H | C₂H₅ | " | " | $n_D^{25.5}$ 1.5657 |
| 207 | " | " |  | " | " | |
| 208 | " | " | CH₂SCH₃ | " | " | |
| 209 | " | " | CH₂OCH₃ | " | " | |
| 210 | " | " | C₃H₇(i) | " | " | |
| 211 | " | " | C₄H₉(t) | " | " | |
| 212 | 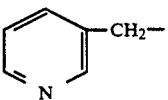 | C₂H₅ | H | N | CN | |
| 213 | " | " | CH₃ | " | " | $n_D^{24.5}$ 1.5665 |
| 214 | " | " | CH₂Cl | " | " | |
| 215 | " | " | C₂H₅ | " | " | |
| 216 | " | C₃H₇(i) | H | " | " | |
| 217 | " | " | CH₃ | " | " | |
| 218 | " | " | C₂H₅ | " | " | |
| 219 | " | COCH₃ | H | " | " | |
| 220 | " | " | CH₃ | " | " | |
| 221 | " | SO₂CH₃ | H | " | " | |
| 222 | " | " | CH₃ | " | " | |
| 223 | 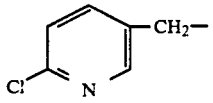 | H | H | N | NO₂ | |
| 224 | " | " | CH₃ | " | " | |
| 225 | " | " | CH₂Cl | " | " | |
| 226 | " | " | CH₂F | " | " | |
| 227 | " | " | C₂H₅ | " | " | |
| 228 | " | " |  | " | " | |
| 229 | " | " | CH₂SCH₃ | " | " | |
| 230 | " | " | CH₂OCH₃ | " | " | |
| 231 | " | " | C₃H₇(i) | " | " | |
| 232 | " | " | C₄H₉(t) | " | " | |
| 233 | " | " | CH=CH₂ | " | " | |
| 234 | " | " | 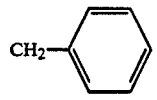 | " | " | |
| 235 | 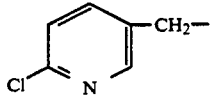 | CH₃ | H | N | NO₂ | |
| 236 | " | " | CH₃ | " | " | $n_D^{25}$ 1.5808 |
| 237 | " | " | CH₂Cl | " | " | |
| 238 | " | " | CH₂F | " | " | |
| 239 | " | " | C₂H₅ | " | " | |

TABLE 1-continued

Structure Formula $$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 240 | " | " |  | " | " | |
| 241 | " | " | CH₂SCH₃ | " | " | |
| 242 | " | " | CH₂OCH₃ | " | " | |
| 243 | " | " | C₃H₇(n) | " | " | |
| 244 | " | " | C₄H₉(t) | " | " | |
| 245 | " | " | CH=CH₂ | " | " | |
| 246 | " | " | CH₂-C₆H₅ | " | " | |
| 247 | 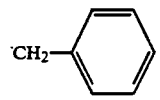 (2-Cl-pyridin-5-yl)CH₂- | C₂H₅ | H | N | NO₂ | |
| 248 | " | " | CH₃ | " | " | |
| 249 | " | " | C₂H₅ | " | " | |
| 250 | " | C₃H₇(i) | H | " | " | |
| 251 | " | " | CH₃ | " | " | |
| 252 | " | " | C₂H₅ | " | " | |
| 253 | " | 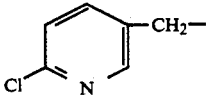 cyclopropyl | H | " | " | |
| 254 | " | " | CH₃ | " | " | |
| 255 | " | " | C₂H₅ | " | " | |
| 256 | " | COCH₃ | H | " | " | |
| 257 | " | " | CH₃ | " | " | |
| 258 | " | SO₂CH₃ | H | " | " | |
| 259 | " | " | CH₃ | " | " | |
| 260 |  (2-Br-pyridin-5-yl)CH₂- | H | CH₃ | N | NO₂ | |
| 261 | " | CH₃ | " | " | " | |
| 262 | (2-F-pyridin-5-yl)CH₂- | H | " | " | " | |
| 263 | " | CH₃ | " | " | " | |
| 264 | (2-CH₃-pyridin-5-yl)CH₂- | H | " | " | " | |
| 265 | " | CH₃ | " | " | " | |
| 266 | 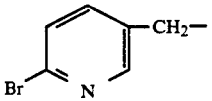 (2-CCl₃-pyridin-5-yl)CH₂- | H | " | " | " | |
| 267 | " | CH₃ | " | " | " | |

TABLE 1-continued

Structure Formula $$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 268 | 5-(CH₂−)-2-(F₃C)-pyridine | H | " | " | " | |
| 269 | " | CH₃ | " | " | " | |
| 270 | 5-(CH₂−)-2-(F₃CO)-pyridine | H | " | " | " | |
| 271 | " | CH₃ | " | " | " | |
| 272 | 5-(CH₂−)-2-(CH₃O)-pyridine | H | CH₃ | N | NO₂ | |
| 273 | " | CH₃ | " | " | " | |
| 274 | 5-(CH₂−)-2-(F₂HCO)-pyridine | H | " | " | " | |
| 275 | " | CH₃ | " | " | " | |
| 276 | 5-(CH₂−)-2-(CH₃O)-pyridine | H | " | " | " | |
| 277 | " | CH₃ | " | " | " | |
| 278 | 5-(CH₂−)-2-(CH₃S)-pyridine | H | " | " | " | |
| 279 | " | CH₃ | " | " | " | |
| 280 | 5-(CH₂−)-2-(CH₃SO₂)-pyridine | H | " | " | " | |
| 281 | " | CH₃ | " | " | " | |
| 282 | 5-(CH₂−)-2-(phenoxy)-pyridine | H | " | " | " | |
| 283 | " | CH₃ | " | " | " | |
| 284 | 5-(CH₂−)-2-(NC)-pyridine | H | CH₃ | N | NO₂ | |

TABLE 1-continued

Structure Formula $$R_1X-N(R_2)-C(R_3)=Z-R^4$$

| Compound No. | R₁X | R₂ | R₃ | Z | R₄ | Physical Properties [ ] m.p. °C. |
|---|---|---|---|---|---|---|
| 285 | " | CH₃ | " | " | " | |
| 286 | 5-(2-nitropyridyl)-CH₂— | H | " | " | " | |
| 287 | " | CH₃ | " | " | " | |
| 288 | 2,4-dichloropyridin-5-yl-CH₂— | H | " | " | " | |
| 289 | " | CH₃ | " | " | " | |
| 290 | 6-chloro-2-methylpyridin-3-yl-CH₂— | H | " | " | " | |
| 291 | " | CH₃ | " | " | " | |
| 292 | 6-(dimethylamino)pyridin-3-yl-CH₂— | H | " | " | " | |
| 293 | " | CH₃ | " | " | " | |
| 294 | pyrazin-2-yl-CH₂— | H | CH₃ | N | NO₂ | |
| 295 | " | CH₃ | " | " | " | |
| 296 | 5-chloropyrazin-2-yl-CH₂— | H | " | " | " | |
| 297 | " | CH₃ | " | " | " | |
| 298 | 5-methylpyrazin-2-yl-CH₂— | H | " | " | " | |
| 299 | " | CH₃ | " | " | " | |
| 300 | 6-chloropyrazin-3-yl-CH₂— | H | " | " | " | |
| 301 | " | CH₃ | " | " | " | |

TABLE 1-continued

Structure Formula:

$$R_1X-N(R_2)-C(R_3)=Z(R_4)$$

| Compound No. | R₁X | R₂ | R₃ | Z | R₄ | Physical Properties [ ] m.p. °C. |
|---|---|---|---|---|---|---|
| 302 | 4-pyrimidinyl-CH₂— | H | " | " | " | |
| 303 | " | CH₃ | " | " | " | |
| 304 | 2-methyl-4-pyrimidinyl-CH₂— | H | " | " | " | |
| 305 | 2-methyl-4-pyrimidinyl-CH₂— | CH₃ | CH₃ | N | NO₂ | |
| 306 | 5-pyrimidinyl-CH₂— | H | " | " | " | |
| 307 | " | CH₃ | " | " | " | |
| 308 | 2-methyl-5-pyrimidinyl-CH₂— | H | " | " | " | |
| 309 | " | CH₃ | " | " | " | |
| 310 | 3-pyridazinyl-CH₂— | H | " | " | " | |
| 311 | " | CH₃ | " | " | " | |
| 312 | 6-chloro-3-pyridazinyl-CH₂— | H | " | " | " | |
| 313 | " | CH₃ | " | " | " | |
| 314 | 2-thiazolyl-CH₂— | H | CH₃ | N | NO₂ | |
| 315 | " | CH₃ | " | " | " | |
| 316 | 2-methyl-thiazolyl-CH₂— | H | " | " | " | |
| 317 | " | CH₃ | " | " | " | |

TABLE 1-continued

Structure Formula $$R_1X-\underset{R_2}{N}-\underset{\|}{C}(R_3)=Z-R^4$$

| Compound No. | R₁X | R₂ | R₃ | Z | R₄ | Physical Properties [ ] m.p. °C. |
|---|---|---|---|---|---|---|
| 318 | 2-chlorothiazol-5-yl-CH₂— | H | " | " | " | |
| 319 | " | CH₃ | " | " | " | |
| 320 | " | " | C₂H₅ | " | " | |
| 321 | " | C₂H₅ | CH₃ | " | " | |
| 322 | 2-chloro-4-methylthiazol-5-yl-CH₂— | H | " | " | " | |
| 323 | " | CH₃ | " | " | " | |
| 324 | pyridin-3-yl-CH₂CH₂— | H | CH₃ | N | NO₂ | |
| 325 | " | CH₃ | " | " | " | |
| 326 | 6-chloropyridin-3-yl-CH₂CH₂— | H | " | " | " | |
| 327 | " | CH₃ | " | " | " | |
| 328 | pyridin-3-yl-CH₂CH₂— | H | " | " | " | |
| 329 | " | CH₃ | " | " | " | |
| 330 | 6-chloropyridin-2-yl-CH₂CH₂— | H | " | " | " | |
| 331 | " | CH₃ | " | " | " | |
| 332 | 1-(6-chloropyridin-3-yl)ethyl— | H | " | " | " | |
| 333 | " | CH₃ | " | " | " | |
| 334 | pyridin-4-yl-CH₂— | H | " | " | " | |
| 335 | " | CH₃ | " | " | " | |
| 336 | pyridin-3-yl-CH₂— | H | H | N | NO₂ | |

TABLE 1-continued

Structure Formula $R_1X-N(R_2)-C(R_4)(Z)=... R_3$ (as depicted)

| Compound No. | R₁X | R₂ | R₃ | Z | R₄ | Physical Properties [ ] m.p. °C. |
|---|---|---|---|---|---|---|
| 337 | " | " | CH₃ | " | " | |
| 338 | " | " | C₂H₅ | " | " | |
| 339 | " | " | CH₂Cl | " | " | |
| 340 | " | " | CH₂F | " | " | |
| 341 | " | " | ▷ (cyclopropyl) | " | " | |
| 342 | " | " | CH₂SCH₃ | " | " | |
| 343 | " | " | CH₂OCH₃ | " | " | |
| 344 | 3-pyridyl-CH₂— | CH₃ | H | N | NO₂ | |
| 345 | " | " | CH₃ | " | " | |
| 346 | " | " | CH₂Cl | " | " | |
| 347 | " | " | CH₂F | " | " | |
| 348 | " | " | C₂H₅ | " | " | |
| 349 | " | " | ▷ (cyclopropyl) | " | " | |
| 350 | " | " | CH₂SCH₃ | " | " | |
| 351 | " | " | CH₂OCH₃ | " | " | |
| 352 | " | " | C₃H₇(i) | " | " | |
| 353 | " | " | C₄H₉(t) | " | " | |
| 354 | 3-pyridyl-CH₂— | C₂H₅ | H | N | NO₂ | |
| 355 | " | " | CH₃ | " | " | |
| 356 | " | " | CH₂Cl | " | " | |
| 357 | " | " | C₂H₅ | " | " | |
| 358 | " | C₃H₇(i) | H | " | " | |
| 359 | " | " | CH₃ | " | " | |
| 360 | " | " | C₂H₅ | " | " | |
| 361 | " | COCH₃ | H | " | " | |
| 362 | " | " | CH₃ | " | " | |
| 363 | " | SO₂CH₃ | H | " | " | |
| 364 | " | " | CH₃ | " | " | |
| 365 | 6-chloro-3-pyridyl-CH₂— | H | H | CH | NO₂ | [116–118] |
| 366 | " | " | CH₃ | " | " | [133–135] |
| 367 | " | " | CH₂Cl | " | " | |
| 368 | " | " | C₂H₅ | " | " | [95–98] |
| 369 | " | " | C₃H₇(i) | " | " | [150–152] |
| 370 | " | " | C₄H₇(t) | " | " | |
| 371 | " | " | CH=CH₂ | " | " | |
| 372 | " | " | CH=CHCH₃ | " | " | |
| 373 | " | " | CH₂CN | " | " | |
| 374 | " | " | CH₂NO₂ | " | " | |
| 375 | " | " | CH₂COOC₂H₅ | " | " | |
| 376 | 6-chloro-3-pyridyl-CH₂— | H | cyclohexyl | CH | NO₂ | |

TABLE 1-continued
Structure Formula
$$R_1X-N(R_2)-C(R_3)=Z-R^4$$
| Compound No. | R₁X | R₂ | R₃ | Z | R₄ | Physical Properties [ ] m.p. °C. |
|---|---|---|---|---|---|---|
| 377 | " | " |  | " | " | |
| 378 | " | " | 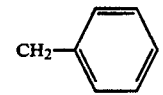 | " | " | |
| 379 | " | " | 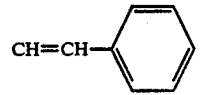 | " | " | |
| 380 | " | CH₃ | H | " | " | |
| 381 | " | " | CH₃ | " | " | [79-82] |
| 382 | " | " | CH₂Cl | " | " | |
| 383 | " | " | C₂H₅ | " | " | [101-104] |
| 384 | " | " | C₃H₇(i) | " | " | |
| 385 | " | " | C₄H₇(t) | " | " | |
| 386 | " | " | CH=CH₂ | " | " | |
| 387 | " | " | CH=CHCH₃ | " | " | |
| 388 | 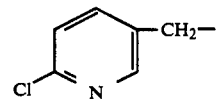 | CH₃ | CH₂CN | CH | NO₂ | |
| 389 | " | " | CH₂NO₂ | " | " | |
| 390 | " | " | CH₂COOC₂H₅ | " | " | |
| 391 | " | " | 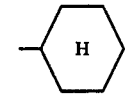 | " | " | |
| 392 | " | " |  | " | " | |
| 393 | " | " | 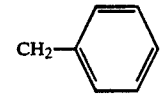 | " | " | |
| 394 | " | " | 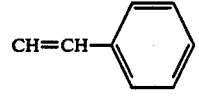 | " | " | |
| 395 | " | C₂H₅ | H | " | " | |
| 396 | " | " | CH₃ | " | " | |
| 397 | " | " | C₂H₅ | " | " | |
| 398 | " | C₃H₇(i) | H | " | " | |
| 399 | " | " | CH₃ | " | " | |
| 400 | 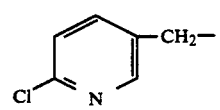 | C₃H₇(i) | C₂H₅ | CH | NO₂ | |
| 401 | " | " |  | H | " | " |

TABLE 1-continued

Structure Formula $$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 402 | " | " | CH₃ | " | " | |
| 403 | " | " | C₂H₅ | " | " | |
| 404 | " | CH₂CH=CH₂ | H | " | " | |
| 405 | " | " | CH₃ | " | " | |
| 406 | " | " | C₂H₅ | " | " | |
| 407 | " | (phenyl) | H | " | " | |
| 408 | " | " | CH₃ | " | " | |
| 409 | " | " | C₂H₅ | " | " | |
| 410 | " | CHO | H | " | " | |
| 411 | " | " | CH₃ | " | " | |
| 412 | 2-Cl-pyridin-5-yl-CH₂— | CHO | C₂H₅ | CH | NO₂ | |
| 413 | " | COCH₃ | H | " | " | |
| 414 | " | " | CH₃ | " | " | |
| 415 | " | " | C₂H₅ | " | " | |
| 416 | " | SO₂CH₃ | H | " | " | |
| 417 | " | " | CH₃ | " | " | |
| 418 | " | " | C₂H₅ | " | " | |
| 419 | " | COOC₂H₅ | H | " | " | |
| 420 | " | " | CH₃ | " | " | |
| 421 | " | " | C₂H₅ | " | " | |
| 422 | " | OC₂H₅ | H | " | " | |
| 423 | " | " | CH₃ | " | " | |
| 424 | " | " | C₂H₅ | " | " | |
| 425 | " | CH₂C≡CH | H | " | " | |
| 426 | " | " | CH₃ | " | " | |
| 427 | " | " | C₂H₅ | " | " | |
| 428 | 2-Br-pyridin-5-yl-CH₂— | H | CH₃ | CH | NO₂ | |
| 429 | " | CH₃ | " | " | " | |
| 430 | 2-F-pyridin-5-yl-CH₂— | H | " | " | " | |
| 431 | " | CH₃ | " | " | " | |
| 432 | 2-CH₃-pyridin-5-yl-CH₂— | H | " | " | " | |
| 433 | " | CH₃ | " | " | " | |
| 434 | 2-Cl₃C-pyridin-5-yl-CH₂— | H | " | " | " | |
| 435 | " | CH₃ | " | " | " | |

TABLE 1-continued

Structure Formula $$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 436 | 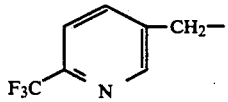 6-(F₃C)-pyridin-3-yl-CH₂— | H | " | " | " | |
| 437 | " | CH₃ | " | " | " | |
| 438 | 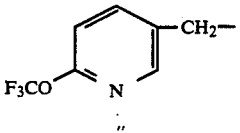 6-(F₃CO)-pyridin-3-yl-CH₂— | H | " | " | " | |
| 439 | " | CH₃ | " | " | " | |
| 440 | 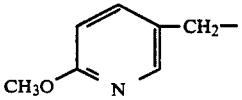 6-(CH₃O)-pyridin-3-yl-CH₂— | H | CH₃ | CH | NO₂ | |
| 441 | " | CH₃ | " | " | " | |
| 442 | 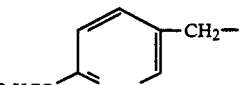 6-(F₂HCO)-pyridin-3-yl-CH₂— | H | " | " | " | |
| 443 | " | CH₃ | " | " | " | |
| 444 | 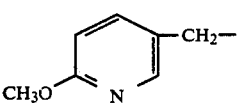 6-(CH₃O)-pyridin-3-yl-CH₂— | H | " | " | " | |
| 445 | " | CH₃ | " | " | " | |
| 446 | 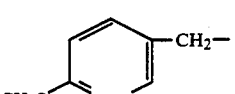 6-(CH₃S)-pyridin-3-yl-CH₂— | H | " | " | " | |
| 447 | " | CH₃ | " | " | " | |
| 448 |  6-(CH₃SO₂)-pyridin-3-yl-CH₂— | H | " | " | " | |
| 449 | " | CH₃ | " | " | " | |
| 450 | 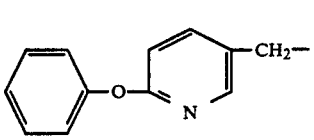 6-(PhO)-pyridin-3-yl-CH₂— | H | " | " | " | |
| 451 | " | CH₃ | " | " | " | |
| 452 | 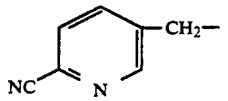 6-(NC)-pyridin-3-yl-CH₂— | H | CH₃ | CH | NO₂ | |

TABLE 1-continued

Structure Formula $$R_1X-N(R_2)-C(R_3)=Z-R^4$$

| Compound No. | R₁X | R₂ | R₃ | Z | R₄ | Physical Properties [ ] m.p. °C. |
|---|---|---|---|---|---|---|
| 453 | " | CH₃ | " | " | " | |
| 454 | 5-(6-nitropyridyl)-CH₂— 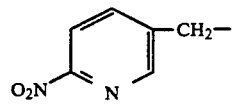 | H | " | " | " | |
| 455 | " | CH₃ | " | " | " | |
| 456 | 5-(2,4-dichloropyridyl)-CH₂— 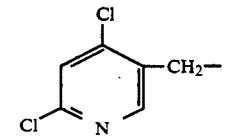 | H | " | " | " | |
| 457 | " | CH₃ | " | " | " | |
| 458 | 3-(6-chloro-2-methylpyridyl)-CH₂— 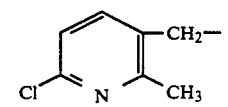 | H | " | " | " | |
| 459 | " | CH₃ | " | " | " | |
| 460 | 5-(6-dimethylaminopyridyl)-CH₂— 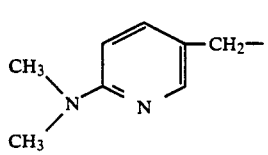 | H | " | " | " | |
| 461 | " | CH₃ | " | " | " | |
| 462 | 2-pyrazinyl-CH₂— 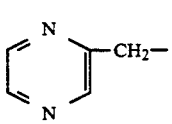 | H | CH₃ | CH | NO₂ | |
| 463 | " | CH₃ | " | " | " | |
| 464 | 5-(2-chloropyrazinyl)-CH₂— 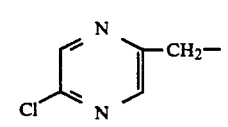 | H | " | " | " | |
| 465 | " | CH₃ | " | " | " | |
| 466 | 5-(2-methylpyrazinyl)-CH₂— 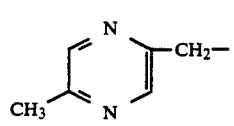 | H | " | " | " | |
| 467 | " | CH₃ | " | " | " | |
| 468 | 5-(2-chloropyrazinyl)-CH₂— 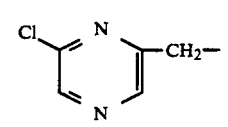 | H | " | " | " | |
| 469 | " | CH₃ | " | " | " | |

TABLE 1-continued

Structure Formula $$R_1X-\underset{R_2}{N}-\underset{\parallel}{\overset{R^4}{\underset{Z}{C}}}-R_3$$

| Compound No. | $R_1X$ | $R_2$ | $R_3$ | $Z$ | $R_4$ | Physical Properties [ ] m.p. °C. |
|---|---|---|---|---|---|---|
| 470 | pyrimidin-4-yl-CH₂— | H | " | " | " | |
| 471 | " | CH₃ | " | " | " | |
| 472 | 2-methylpyrimidin-4-yl-CH₂— | H | " | " | " | |
| 473 | 2-methylpyrimidin-4-yl-CH₂— | CH₃ | CH₃ | CH | NO₂ | |
| 474 | pyrimidin-5-yl-CH₂— | H | " | " | " | |
| 475 | " | CH₃ | " | " | " | |
| 476 | 2-methylpyrimidin-5-yl-CH₂— | H | " | " | " | |
| 477 | " | CH₃ | " | " | " | |
| 478 | pyridazin-3-yl-CH₂— | H | " | " | " | |
| 479 | " | CH₃ | " | " | " | |
| 480 | 6-chloropyridazin-3-yl-CH₂— | H | " | " | " | |
| 481 | " | CH₃ | " | " | " | |
| 482 | thiazol-2-yl-CH₂— | H | " | " | " | |
| 483 | " | CH₃ | " | " | " | |
| 484 | 2-methylthiazol-2-yl-CH₂— | H | CH₃ | CH | NO₂ | |
| 485 | " | CH₃ | " | " | " | |

TABLE 1-continued

Structure Formula:

$$R_1X-N(R_2)-C(R_3)=Z-R_4$$

| Compound No. | R₁X | R₂ | R₃ | Z | R₄ | Physical Properties [ ] m.p. °C |
|---|---|---|---|---|---|---|
| 486 | 2-chloro-thiazol-5-yl-CH₂— | H | " | " | " | |
| 487 | " | CH₃ | " | " | " | |
| 488 | " | " | C₂H₅ | " | " | |
| 489 | " | C₂H₅ | CH₃ | " | " | |
| 490 | pyridin-3-yl-CH₂CH₂— | H | " | " | " | |
| 491 | " | CH₃ | " | " | " | |
| 492 | 6-chloro-pyridin-3-yl-CH₂CH₂— | H | " | " | " | |
| 493 | " | CH₃ | " | " | " | |
| 494 | pyridin-3-yl-CH₂CH₂— | H | " | " | " | |
| 495 | " | CH₃ | " | " | " | |
| 496 | 6-chloro-pyridin-2-yl-CH₂CH₂— | H | CH₃ | CH | NO₂ | |
| 497 | " | CH₃ | " | " | " | |
| 498 | 6-chloro-pyridin-3-yl-CH(CH₃)— | H | " | " | " | |
| 499 | " | CH₃ | " | " | " | |
| 500 | pyridin-4-yl-CH₂ | H | " | " | " | |
| 501 | " | CH₃ | " | " | " | |
| 502 | pyridin-3-yl-CH₂— | H | H | CH | NO₂ | |
| 503 | " | " | CH₃ | " | " | |
| 504 | " | " | CH₂Cl | " | " | |
| 505 | " | " | C₂H₅ | " | " | |
| 506 | " | " | C₃H₇(i) | " | " | |
| 507 | " | " | C₄H₉(t) | " | " | |

TABLE 1-continued

Structure Formula $$R_1X-\underset{R_2}{N}-\overset{\overset{R^4}{\|}Z}{C}-R_3$$

| Compound No. | R₁X | R₂ | R₃ | Z | R₄ | Physical Properties [ ] m.p. °C. |
|---|---|---|---|---|---|---|
| 508 | " | CH₃ | H | " | " | |
| 509 | " | " | CH₃ | " | " | |
| 510 | " | " | CH₂Cl | " | " | |
| 511 | " | " | C₂H₅ | " | " | |
| 512 | " | " | 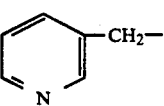 | " | " | |
| 513 | 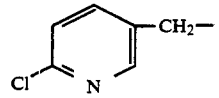 | CH₃ | C₃H₇(i) | CH | NO₂ | |
| 514 | " | " | C₄H₉(t) | " | " | |
| 515 | " | C₂H₅ | H | " | " | |
| 516 | " | " | CH₃ | " | " | |
| 517 | " | " | C₂H₅ | " | " | |
| 518 | " | 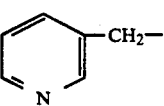 | H | " | " | |
| 519 | " | " | CH₃ | " | " | |
| 520 | " | " | C₂H₅ | " | " | |
| 521 | " | COCH₃ | H | " | " | |
| 522 | " | " | CH₃ | " | " | |
| 523 | " | " | C₂H₅ | " | " | |
| 524 | " | SO₂CH₃ | H | " | " | |
| 525 | " | " | CH₃ | " | " | |
| 526 | " | " | C₂H₅ | " | " | |
| 527 | 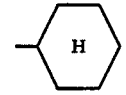 | H | H | CH | CN | |
| 528 | " | " | CH₃ | " | " | [95-98] |
| 529 | " | " | CH₂Cl | " | " | |
| 530 | " | " | C₂H₅ | " | " | |
| 531 | " | " | C₃H₇(i) | " | " | |
| 532 | " | " | C₄H₉(t) | " | " | |
| 533 | " | " | CH=CH₂ | " | " | |
| 534 | " | " | CH=CHCH₃ | " | " | |
| 535 | " | " | CH₂CN | " | " | |
| 536 | " | " | CH₂NO₂ | " | " | |
| 537 | " | " | CH₂COOC₂H₅ | " | " | |
| 538 | 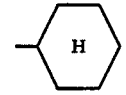 | H | 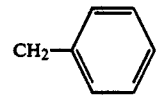 H | CH | CN | |
| 539 | " | " | 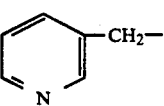 | " | " | |
| 540 | " | " | 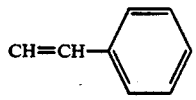 | " | " | |
| 541 | " | " | 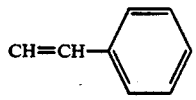 | " | " | |

TABLE 1-continued

Structure Formula $$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 542 | " | CH₃ | H | " | " | |
| 543 | " | " | CH₃ | " | " | $n_D^{29}$ 1.5941 |
| 544 | " | " | CH₂Cl | " | " | |
| 545 | " | " | C₂H₅ | " | " | |
| 546 | " | " | C₃H₇(i) | " | " | |
| 547 | " | " | C₄H₉(t) | " | " | |
| 548 | " | " | CH=CH₂ | " | " | |
| 549 | " | " | CH=CHCH₃ | " | " | |
| 550 | 2-Cl-5-pyridyl-CH₂— | CH₃ | CH₂CN | CH | CN | |
| 551 | " | " | CH₂NO₂ | " | " | |
| 552 | " | " | CH₂COOC₂H₅ | " | " | |
| 553 | " | " | cyclohexyl | " | " | |
| 554 | " | " | cyclopropyl | " | " | |
| 555 | " | " | CH₂-C₆H₅ | " | " | |
| 556 | " | " | CH=CH-C₆H₅ | " | " | |
| 557 | " | C₂H₅ | H | " | " | |
| 558 | " | " | CH₃ | " | " | |
| 559 | " | " | C₂H₅ | " | " | |
| 560 | " | C₃H₇(i) | H | " | " | |
| 561 | " | " | CH₃ | " | " | |
| 562 | 2-Cl-5-pyridyl-CH₂— | C₃H₇(i) | C₂H₅ | CH | CN | |
| 563 | " | cyclopropyl | H | " | " | |
| 564 | " | " | CH₃ | " | " | |
| 565 | " | " | C₂H₅ | " | " | |
| 566 | " | CH₂CH=CH₂ | H | " | " | |
| 567 | " | " | CH₃ | " | " | |
| 568 | " | " | C₂H₅ | " | " | |
| 569 | " | C₆H₅ | H | " | " | |
| 570 | " | " | CH₃ | " | " | |
| 571 | " | " | C₂H₅ | " | " | |
| 572 | " | CHO | H | " | " | |

TABLE 1-continued

Structure Formula $$R_1X-\underset{R_2}{N}-\underset{\|}{C}(R_3)$$ with $Z$ and $R^4$

| Compound No. | R₁X | R₂ | R₃ | Z | R₄ | Physical Properties [ ] m.p. °C. |
|---|---|---|---|---|---|---|
| 573 | " | " | CH₃ | " | " | |
| 574 | 6-chloro-pyridin-3-yl-CH₂— | CHO | C₂H₅ | CH | CN | |
| 575 | " | COCH₃ | H | " | " | |
| 576 | " | " | CH₃ | " | " | |
| 577 | " | " | C₂H₅ | " | " | |
| 578 | " | SO₂CH₃ | H | " | " | |
| 579 | " | " | CH₃ | " | " | |
| 580 | " | " | C₂H₅ | " | " | |
| 581 | " | COOC₂H₅ | H | " | " | |
| 582 | " | " | CH₃ | " | " | |
| 583 | " | " | C₂H₅ | " | " | |
| 584 | " | OC₂H₅ | H | " | " | |
| 585 | " | " | CH₃ | " | " | |
| 586 | " | " | C₂H₅ | " | " | |
| 587 | " | CH₂C≡CH | H | " | " | |
| 588 | " | " | CH₃ | " | " | |
| 589 | " | " | C₂H₅ | " | " | |
| 590 | 6-bromo-pyridin-3-yl-CH₂— | H | CH₃ | CH | CN | |
| 591 | " | CH₃ | " | " | " | |
| 592 | 6-fluoro-pyridin-3-yl-CH₂— | H | " | " | " | |
| 593 | " | CH₃ | " | " | " | |
| 594 | 6-methyl-pyridin-3-yl-CH₂— | H | " | " | " | |
| 595 | " | CH₃ | " | " | " | |
| 596 | 6-trichloromethyl-pyridin-3-yl-CH₂— | H | " | " | " | |
| 597 | " | CH₃ | " | " | " | |
| 598 | 6-trifluoromethyl-pyridin-3-yl-CH₂— | H | " | " | " | |
| 599 | " | CH₃ | " | " | " | |
| 600 | 6-trifluoromethoxy-pyridin-3-yl-CH₂— | H | " | " | " | |
| 601 | " | CH₃ | " | " | " | |

TABLE 1-continued

Structure Formula:

$$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 602 | 5-(CH₂-)-2-(CH₃O)-pyridine | H | CH₃ | CH | CN | |
| 603 | " | CH₃ | " | " | " | |
| 604 | 5-(CH₂-)-2-(F₂HCO)-pyridine | H | " | " | " | |
| 605 | " | CH₃ | " | " | " | |
| 606 | 5-(CH₂-)-2-(CH₃O)-pyridine | H | " | " | " | |
| 607 | " | CH₃ | " | " | " | |
| 608 | 5-(CH₂-)-2-(CH₃S)-pyridine | H | " | " | " | |
| 609 | " | CH₃ | " | " | " | |
| 610 | 5-(CH₂-)-2-(CH₃SO₂)-pyridine | H | " | " | " | |
| 611 | " | CH₃ | " | " | " | |
| 612 | 5-(CH₂-)-2-(phenoxy)-pyridine | H | " | " | " | |
| 613 | " | CH₃ | " | " | " | |
| 614 | 5-(CH₂-)-2-(NC)-pyridine | H | CH₃ | CH | CN | |
| 615 | " | CH₃ | " | " | " | |
| 616 | 5-(CH₂-)-2-(O₂N)-pyridine | H | " | " | " | |
| 617 | " | CH₃ | " | " | " | |

TABLE 1-continued

Structure Formula $$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 618 | 4,6-dichloropyridin-3-yl-CH₂— | H | " | " | " | |
| 619 | " | CH₃ | " | " | " | |
| 620 | 6-chloro-2-methylpyridin-3-yl-CH₂— | H | " | " | " | |
| 621 | " | CH₃ | " | " | " | |
| 622 | 6-(dimethylamino)pyridin-3-yl-CH₂— | H | " | " | " | |
| 623 | " | CH₃ | " | " | " | |
| 624 | pyrazin-2-yl-CH₂— | H | CH₃ | CH | CN | |
| 625 | " | CH₃ | " | " | " | |
| 626 | 5-chloropyrazin-2-yl-CH₂— | H | " | " | " | |
| 627 | " | CH₃ | " | " | " | |
| 628 | 5-methylpyrazin-2-yl-CH₂— | H | " | " | " | |
| 629 | " | CH₃ | " | " | " | |
| 630 | 6-chloropyrazin-2-yl-CH₂— | H | " | " | " | |
| 631 | " | CH₃ | " | " | " | |
| 632 | pyrimidin-4-yl-CH₂— | H | " | " | " | |
| 633 | " | CH₃ | " | " | " | |

TABLE 1-continued
Structure Formula
$$\begin{array}{c} R^4 \\ | \\ Z \\ \| \\ R_1X-N-C-R_3 \\ | \\ R_2 \end{array}$$
| Compound No. | R₁X | R₂ | R₃ | Z | R₄ | Physical Properties [ ] m.p. °C. |
|---|---|---|---|---|---|---|
| 634 | 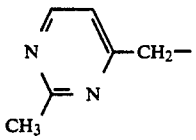 | H | " | " | " | |
| 635 | 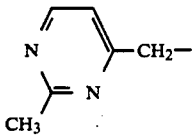 | CH₃ | CH₃ | CH | CN | |
| 636 | 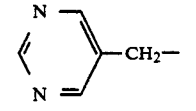 | H | " | " | " | |
| 637 | " | CH₃ | " | " | " | |
| 638 | 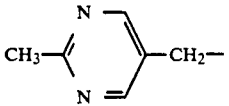 | H | " | " | " | |
| 639 | " | CH₃ | " | " | " | |
| 640 | 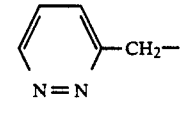 | H | " | " | " | |
| 641 | " | CH₃ | " | " | " | |
| 642 | 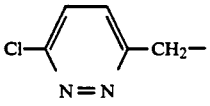 | H | " | " | " | |
| 643 | " | CH₃ | " | " | " | |
| 644 | 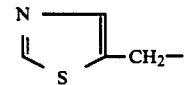 | H | CH₃ | CH | CN | |
| 645 | " | CH₃ | " | " | " | |
| 646 | 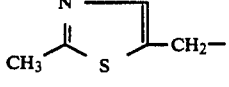 | H | " | " | " | |
| 647 | " | CH₃ | " | " | " | |
| 648 | 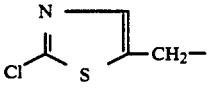 | H | " | " | " | |
| 649 | " | CH₃ | " | " | " | |
| 650 | " | " | C₂H₅ | " | " | |
| 651 | " | C₂H₅ | CH₃ | " | " | |

TABLE 1-continued

Structure Formula:
$$R_1X-N(R_2)-C(R_3)=Z-R_4$$

| Compound No. | R₁X | R₂ | R₃ | Z | R₄ | Physical Properties [ ] m.p. °C. |
|---|---|---|---|---|---|---|
| 652 | 3-pyridyl-CH₂CH₂- | H | CH₃ | CH | CN | |
| 653 | " | CH₃ | " | " | " | |
| 654 | 2-Cl-5-pyridyl-CH₂CH₂- | H | " | " | " | |
| 655 | " | CH₃ | " | " | " | |
| 656 | 4-pyridyl-CH₂CH₂- | H | " | " | " | |
| 657 | " | CH₃ | " | " | " | |
| 658 | 6-Cl-2-pyridyl-CH₂CH₂- | H | " | " | " | |
| 659 | " | CH₃ | " | " | " | |
| 660 | 2-Cl-5-pyridyl-CH(CH₃)- | H | " | " | " | |
| 661 | " | CH₃ | " | " | " | |
| 662 | 4-pyridyl-CH₂- | H | " | " | " | |
| 663 | " | CH₃ | " | " | " | |
| 664 | 3-pyridyl-CH₂- | H | H | CH | CN | |
| 665 | " | " | CH₃ | " | " | |
| 666 | " | " | CH₂Cl | " | " | |
| 667 | " | " | C₂H₅ | " | " | |
| 668 | " | " | C₃H₇(i) | " | " | |
| 669 | " | " | C₄H₉(t) | " | " | |
| 670 | " | CH₃ | H | " | " | |
| 671 | " | " | CH₃ | " | " | |
| 672 | " | " | CH₂Cl | " | " | |
| 673 | " | " | C₂H₅ | " | " | |
| 674 | " | " | cyclopropyl | " | " | |

TABLE 1-continued

Structure Formula $$R_1X-\underset{\underset{R_2}{|}}{N}-\underset{\underset{Z}{\|}}{\overset{R^4}{\overset{|}{C}}}-R_3$$

| Compound No. | R₁X | R₂ | R₃ | Z | R₄ | Physical Properties [ ] m.p. °C. |
|---|---|---|---|---|---|---|
| 675 | 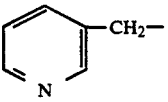 | CH₃ | C₃H₇(i) | CH | CN | |
| 676 | " | " | C₄H₉(t) | " | " | |
| 677 | " | C₂H₅ | H | " | " | |
| 678 | " | " | CH₃ | " | " | |
| 679 | " | " | C₂H₅ | " | " | |
| 680 | " | 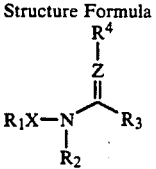 | H | " | " | |
| 681 | " | " | CH₃ | " | " | |
| 682 | " | " | C₂H₅ | " | " | |
| 683 | " | COCH₃ | H | " | " | |
| 684 | " | " | CH₃ | " | " | |
| 685 | " | " | C₂H₅ | " | " | |
| 686 | " | SO₂CH₃ | H | " | " | |
| 687 |  | SO₂CH₃ | CH₃ | CH | CN | |
| 688 | " | " | C₂H₅ | " | " | |

*1 ¹H-NMR(CDCl₃) δ; ppm 3.32(s, 3H), 4.63(s, 2H), 7.37(d, 1H), 7.62(dd, 1H), 8.37(d, 1H)

The compounds of this invention exhibit high insecticidal activities against various species of insect pests such as cutworms, diamondback moth, aphids, leafhoppers and planthoppers. In recent years the decrease of the control effects of organophosphorus and carbamate insecticides, which is caused by the development of resistance to these insecticides, has become serious problem. In such situations, the development of new insecticides which is effective on the resistant pests has been desired. The compounds of this invention possess superior insecticidal activities against not only susceptible strains but also resistant ones.

The insecticides covered by this invention contain as active ingredients one or more types of the compounds as expressed by the general formula (1). These active ingredients, may be used as produced but normally they are used in any of the forms which ordinary agricultural chemicals can take, namely wettable powder, dust, emulsifiable concentrate, suspension concentrates, smoking chemicals, fumigant, granule, or other formulations. For additives and carriers are used soybean flour, wheat flour or other vegetable flours, diatomaceous earth, apatite, gypsum, talc, pyrophyllite, clay or other fine mineral powders, when solid formulations are intended.

When liquid formulations are intended, then for solvents are used kerosene, mineral oil, petroleum, solvent naphtha, xylene, cyclohexane, cyclohexanone, dimethylformamide, dimethylsulfoxide, alcohol, acetone, water, etc. A surface active agent may, if necessary, be added in order to give a homogeneous and suitable formulation. The wettable powders, emulsifiable concentrates, suspension concentrates, etc. thus obtained are diluted with water into suspensions or emulsions of a prescribed concentration, before they are actually sprayed on plants in the field. In the case of dusts or granules, they are directly applied without further processing.

It goes without saying that the compound(s) of this invention is effective even alone, but it can be used by mixing with various types of insecticides, acaricides and fungicides.

Typical examples of acaricides and insecticides which can be used by mixing with the compounds of this invention are described below:

Acaricides (fungicides): chlorobenzilate, chloropropylate, proclonol, bromopropylate, dicofol, dinobuton, binapacryl, chlordimeform, amitraz, propargite, PPPS, benzoximate, hexythiazox, fenbutatin oxide, polynactine, chinomethionat, thioquinox, chlorfenson, tetradifon, phenproxide, avermectins, clofentezine, flubenzimine, fenazaquin, pyridaben, fenproximate, chlorfenethol, thiophanate-methyl, benomyl, thiram, iprobenfos, edifenfos, fthalide, probenazole, isoprothiolane, chorothalonil, captan, polyoxin-B, blasticidin-S, kasugamycin, validamycin, tricyclazole, pyroquilon, phenazine oxide, mepronil, flutolanil, pencycuron, iprodione, hymexazole, metalaxyl, triflumizole, diclomezine, tecloftalam, vinclozolin, procymidone, bitertanol, triadimefon, prochloraz, pyrifenox, fenarimal, fenpropimorph, triforine, metalaxyl, oxycarboxin, pefrazoate, diclomedine, fluazinam, oxadixyl, ethoquinolac, TPTH, propamocarb, fosetyl, dihydrostreptomycin, anilazine, dithianon, diethofencarb. Organophosphorus-type and carbamate-type insecticides (acaridides):

fenthion, fenitrothion, diazinon, chlorpyrifos, oxydeprofos, vamidothion, phenthoate, dimethoate, formothion, malathion, trichlorfon, thiometon, phosmet, menazon, dichlorvos, acephate, EPBP, dialifos, parathion-methyl, oxydemeton-methyl, ethion, aldicarb, propoxur, methomyl, fenobucarb, BPMC, pyraclofos, monocrotophos, salithion, cartap, carbosulfan carbofuran, benfuracarb, metolcarb, carbaryl, pirimicarb, ethiofencarb, fenoxycarb, Pyrethroide-type insecticides (acaricides): permethrin, cypermethrin, deltamethrin, fenvalerate, fenpropathrin, pyrethrins, allethrin, tetramethrin, resmethrin, parthrin, dimethrin, proparthrin, bifenthrin, prothrin, fluvalinate, cyfluthrin, cyhalothrin, flucythrinate, ethofenprox, cycloprothrin, tralomethrin, silaneophan. Benzoylphenylurea-type and other types insecticides: diflubenzuron, chlorfluazuron, triflumuron, teflubenzuron, buprofezin, pyriproxyfen, flufenoxuron, Machine oil.

Same examples of the formulations are given below. The carriers, surface-active agents, etc. that are added, however, are not limited to these Examples.

EXAMPLE 7

Emulsifiable concentrate

| | |
|---|---|
| The compound of this invention | 10 parts |
| Alkylphenyl polyoxyethylene | 5 parts |
| Dimethyl formamide | 50 parts |
| Xylene | 35 parts |

These components are mixed and dissolved and, for use in spraying, the liquid mixture is water-diluted into an emulsion.

EXAMPLE 8

Wettable powder

| | |
|---|---|
| The compound of this invention | 20 parts |
| Higher alcohol sulfuric ester | 5 parts |
| Diatomaceous earth | 70 parts |
| Silica | 5 parts |

These components are mixed and ground to fine powder, which for use in spraying, are water-diluted into a suspension.

EXAMPLE 9

Dust

| | |
|---|---|
| The compound of this invention | 5 parts |
| Talc | 94.7 parts |
| Silica | 0.3 parts |

These are mixed and ground and used as-ground in spraying.

EXAMPLE 10

Granule

| | |
|---|---|
| The compound of this invention | 5 parts |
| Clay | 73 parts |
| Bentonite | 20 parats |
| Sodium dioctylsulfosuccinate | 1 part |
| Sodium phosphate | 1 part |

The above compounds are granulated, and applied as it is when used.

Industrial applicability

The tests below show the insecticidal activity of the compounds of this invention.

TEST 1

Efficacy for cotton aphid 30 to 50 insects of cotton aphid per plot were inoculated using a small brush on cucumber leaves which were seeded in pots, 10 cm in diameter, and 10 days old after germination. A day later, wounded insect pests were removed, and a chemical solution, which was prepared in the way that the emulsifiable concentrate described in Example 7 of the above example of insecticide was diluted with water to 125 ppm of compound concentration according to the prescription, was sprayed. The pots were placed in a thermostatic room at temperature of 25° C. and humidity of 65%. The number of survival pests was counted 7 days later and the control efficacy was calculated by comparing with that of untreated plot. The results are shown in Table 2.

TABLE 2

| Compound No. | Control Efficacy (7 days later) 125 ppm |
|---|---|
| 1 | 100% |
| 2 | 100 |
| 3 | 100 |
| 4 | 100 |
| 6 | 100 |
| 8 | 100 |
| 10 | 100 |
| 16 | 100 |
| 20 | 100 |
| 21 | 100 |
| 22 | 100 |
| 23 | 100 |
| 24 | 100 |
| 25 | 100 |
| 27 | 100 |
| 29 | 100 |
| 31 | 100 |
| 32 | 100 |
| 33 | 100 |
| 38 | 100 |
| 44 | 100 |
| 48 | 100 |
| 50 | 100 |
| 51 | 100 |
| 53 | 100 |
| 57 | 100 |
| 60 | 100 |
| 62 | 100 |
| 64 | 100 |
| 66 | 100 |
| 68 | 100 |
| 70 | 100 |
| 72 | 100 |
| 73 | 100 |
| 74 | 100 |
| 78 | 100 |
| 80 | 100 |
| 82 | 100 |
| 84 | 100 |
| 86 | 100 |
| 88 | 100 |
| 92 | 100 |
| 96 | 100 |
| 100 | 100 |
| 102 | 100 |
| 115 | 100 |
| 116 | 100 |
| 120 | 100 |
| 124 | 100 |
| 130 | 100 |

TABLE 2-continued

| Compound No. | Control Efficacy (7 days later) 125 ppm |
|---|---|
| 132 | 100 |
| 136 | 100 |
| 144 | 100 |
| 145 | 100 |
| 146 | 100 |
| 148 | 100 |
| 149 | 100 |
| 150 | 100 |
| 151 | 100 |
| 152 | 100 |
| 163 | 100 |
| 164 | 100 |
| 169 | 100 |
| 170 | 100 |
| 171 | 100 |
| 172 | 100 |
| 173 | 100 |
| 174 | 100 |
| 177 | 100 |
| 178 | 100 |
| 188 | 100 |
| 189 | 100 |
| 190 | 100 |
| 194 | 100 |
| 203 | 100 |
| 206 | 100 |
| 213 | 100 |
| 236 | 100 |
| 366 | 100 |
| 368 | 100 |
| 381 | 100 |
| 383 | 100 |
| 543 | 100 |
| Comparative compound A | 27 |
| Comparative compound B | 100 |

Comparative compound A:

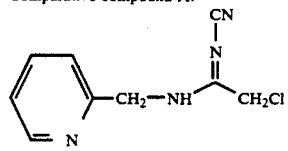

Comparative compound B:

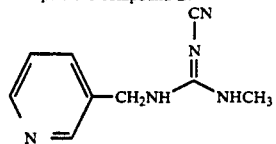

TEST 2

Efficacy for green rice leafhopper

Rice seedlings of 7 days old after germination were immersed in a chemical solution, which was prepared in the way that the emulsifiable concentrate described in Example 7 of the above example of insecticide was diluted with water to 125 ppm of compound concentration according to prescription, for 30 seconds. After dried in air, the treated seedlings were placed in test tubes and 10 insects of 3rd-instar larvae of green rice leafhopper resistant to the organophosphorus and carbamate insecticides were inoculated. The tubes were covered with gauze, and placed in a thermostatic room at temperature of 25° C. and humidity of 65%. The mortality was checked 5 days later. The results are shown in Table 3.

TABLE 3

| Compound No. | % mortality (5 days later) 125 ppm |
|---|---|
| 1 | 100% |

TABLE 3-continued

| Compound No. | % mortality (5 days later) 125 ppm |
|---|---|
| 2 | 100 |
| 4 | 100 |
| 6 | 100 |
| 8 | 100 |
| 10 | 100 |
| 16 | 100 |
| 18 | 100 |
| 20 | 100 |
| 21 | 100 |
| 22 | 100 |
| 23 | 100 |
| 24 | 100 |
| 25 | 100 |
| 27 | 100 |
| 28 | 100 |
| 29 | 100 |
| 31 | 100 |
| 32 | 100 |
| 33 | 100 |
| 35 | 100 |
| 36 | 100 |
| 44 | 100 |
| 48 | 100 |
| 50 | 100 |
| 51 | 100 |
| 53 | 100 |
| 57 | 100 |
| 60 | 100 |
| 62 | 100 |
| 66 | 100 |
| 68 | 100 |
| 72 | 100 |
| 73 | 100 |
| 74 | 100 |
| 78 | 100 |
| 82 | 100 |
| 84 | 100 |
| 86 | 100 |
| 88 | 100 |
| 92 | 100 |
| 96 | 100 |
| 100 | 100 |
| 102 | 100 |
| 116 | 100 |
| 120 | 100 |
| 124 | 100 |
| 130 | 100 |
| 132 | 100 |
| 136 | 100 |
| 144 | 100 |
| 146 | 100 |
| 148 | 100 |
| 150 | 100 |
| 152 | 100 |
| 164 | 100 |
| 169 | 100 |
| 170 | 100 |
| 171 | 100 |
| 172 | 100 |
| 173 | 100 |
| 174 | 100 |
| 178 | 100 |
| 188 | 100 |
| 190 | 100 |
| 201 | 100 |
| 203 | 100 |
| 213 | 100 |
| 236 | 100 |
| 366 | 100 |
| 368 | 100 |
| 369 | 100 |
| 381 | 100 |
| Comparative Compound A | 0 |
| Comparative Compound B | 0 |

TABLE 3-continued

| Compound No. | % mortality (5 days later) 125 ppm |
|---|---|
| Comparative Compound C | 0 |

Comparative compound A and B: The same as test 1
Compound C:

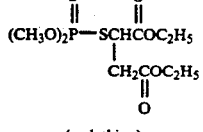

(malathion)

TEST 3

Efficacy for rice armyworm

The test compounds were formulated into the wettable powder in the same manner as Example 8. The compounds were diluted with water to 125 ppm. A maize leaf was immersed in the chemical solution for 30 seconds. After air-dried, the treated leaf was placed in a petri dish and five 3rd-instar larvae of rice armyworm were inoculated. The petri dishes were covered with glass lids, and placed in a thermostatic room at 25° C. and 65% relative humidity. The mortality was checked 5 days later. Two replications were conducted in the each test. The results are shown in Table 4.

TABLE 3

| Compound No. | % mortality (5 days later) 125 ppm |
|---|---|
| 21 | 100% |
| 22 | 100 |
| 23 | 100 |
| 24 | 100 |
| 25 | 100 |
| 51 | 100 |
| 57 | 100 |
| 88 | 100 |
| 92 | 100 |
| 148 | 100 |
| 172 | 100 |
| 381 | 100 |
| Comparative compound A | 0 |
| Comparative compound B | 0 |
| Comparative compound D | 40 |

Comparative compound A and B: The same as Test 1
Compound D:

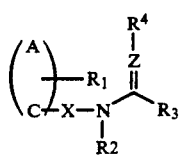

(chlordimeform)

We claim:

1. An insecticidal compound of the formula

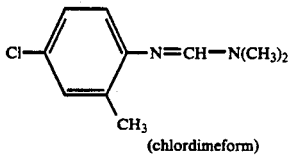

wherein

A completes a 5 or 6 membered aromatic ring having one heteroatomic ring member comprising nitrogen, provided, however, that the ring is not unsubstituted 2-pyridyl;

$R_1$ is hydrogen or $C_{1-5}$alkyl; $C_{1-5}$haloalkyl, $C_{1-5}$alkoxy, $C_{1-5}$alkylthio, $C_{1-5}$alkylsulfonyl, cyano, halogen, or $C_{1-5}$dialkylamino;

X is $C_{1-3}$alkylene or $C_{1-3}$alkylidene;

$R_2$ is hydrogen, carbamoyl, monoalkylcarbamoyl, $C_{1-5}$dialkylcarbamoyl, thiocarbamoyl, monoalkylthiocarbamoyl, sulfamoyl, monoalkylsulfamoyl, $C_{1-5}$dialkylsulfamoyl, $C_{1-5}$alkyl, $C_{2-5}$alkenyl, $C_{2-5}$alkynyl, $C_{3-8}$cycloalkyl, $C_{3-8}$cycloalkenyl, aryl, or the radical

—Y—$R_5$ wherein

Y is O, $S(O)_n$, CO, CS or $CO_2$, n is 0, 1 or 2, $R_5$ is hydrogen, $C_{1-5}$alkyl, $C_{2-5}$alkenyl, $C_{2-5}$alkynyl, $C_{3-8}$cycloalkyl, $C_{3-8}$cycloalkenyl, or aryl;

$R_3$ is hydrogen, $C_{1-5}$alkyl, $C_{2-5}$alkenyl, $C_{2-5}$alkynyl, $C_{3-8}$cycloalkyl, or $C_{3-8}$cycloalkenyl;

$R_4$ is cyano or nitro;

Z is CH or N;

and an insecticidal acceptable salt thereof.

2. An insecticidal compound according to claim 1 wherein the aromatic ring is of the formula

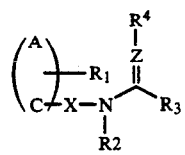

wherein

A completes a 6 membered aromatic ring selected from the group pyridyl;

$R_1$ is hydrogen or $C_{1-5}$alkyl; $C_{1-5}$haloalkyl, $C_{1-5}$alkoxy, $C_{1-5}$alkylthio, $C_{1-5}$alkylsulfonyl, cyano, halogen, or $C_{1-5}$dialkylamino;

X is $C_{1-3}$alkylene or $C_{1-3}$alkylidene;

$R_2$ is hydrogen, monoalkylcarbamoyl, $C_{1-5}$dialkylcarbamoyl, $C_{1-5}$alkyl, $C_{2-5}$alkenyl, $C_{2-5}$alkynyl, $C_{3-6}$cycloalkyl, aryl, or the radical

—Y—$R_5$ wherein

Y is O, CO, $CO_2$ or $SO_2$;

$R_5$ is $C_{1-5}$alkyl or aryl;

$R_3$ is hydrogen, $C_{1-5}$alkyl, or $C_{3-6}$cycloalkyl;

Z is N;

and an insecticidal acceptable salt thereof.

3. N-cyano-N'-(2-chloro-5-pyridylmethyl)-N'-methylacetamidine.

4. 2-(2-chloro-5-pyridylmethylamino)-1-nitro-1-butene.

5. N-cyano-N'-(2-chloro-5-pyridylmethyl)-N'-ethylacetamidine.

6. N-(2-chloro-5-pyridylmethyl)-N-methyl-N'-nitroacetamidine.

7. An insecticidal composition comprising the compound of claim 2 as an active ingredient.

8. An insecticidal composition comprising the compound of claim 3 as an active ingredient.

9. An insecticidal composition comprising the compound of claim 4 as an active ingredient.

10. An insecticidal composition comprising the compound of claim 5 as an active ingredient.

11. Method of controlling both lepidopterous and hemipterous insects by applying to the locus where control is desired an insecticidally effective amount of a compound of claim 1.

12. Method of controlling both lepidopterous and hemipterous insects by applying to the locus where control is desired an insecticidally effective amount of a compound of claim 2.

13. Method of controlling both lepidopterous and hemipterous insects by applying to the locus where control is desired an insecticidally effective amount of the compound of claim 3.

14. Method of controlling both lepidopterous and hemipterous insects by applying to the locus where control is desired an insecticidally effective amount of the compound of claim 4.

15. Method of controlling both lepidopterous and hemipterous insects by applying to the locus where control is desired an insecticidally effective amount of the compound of claim 5.

16. Method of controlling both lepidopterous and hemipterous insects by applying to the locus where control is desired an insecticidally effective amount of the compound of claim 6.

* * * * *